United States Patent
Unger

(10) Patent No.: US 7,641,699 B2
(45) Date of Patent: Jan. 5, 2010

(54) FEMORAL HEAD CALCAR LOADING PROSTHESIS

(76) Inventor: Anthony S. Unger, 5409 Tuscarawes Rd., Bethesda, MD (US) 20816

(*) Notice: Subject to any disclaimer, the term of this patent is extended or adjusted under 35 U.S.C. 154(b) by 67 days.

(21) Appl. No.: 11/763,886

(22) Filed: Jun. 15, 2007

(65) Prior Publication Data

US 2008/0312746 A1 Dec. 18, 2008

(51) Int. Cl.
A61F 2/36 (2006.01)

(52) U.S. Cl. ............... 623/23.35; 623/23.15; 623/23.11

(58) Field of Classification Search ............... 623/22.15, 623/23.11–23.38; A61F 2/36
See application file for complete search history.

(56) References Cited

U.S. PATENT DOCUMENTS

| | | | |
|---|---|---|---|
| 2,934,065 A | 4/1960 | Townley | |
| 3,889,299 A | 6/1975 | Osborne et al. | |
| 4,279,042 A | 7/1981 | Andriacchi et al. | |
| 4,332,036 A | 6/1982 | Sutter et al. | |
| 4,608,055 A | 8/1986 | Morrey et al. | |
| 4,738,681 A | 4/1988 | Koeneman et al. | |
| 4,846,841 A | 7/1989 | Oh | |
| 4,895,573 A | 1/1990 | Koeneman et al. | |
| 5,035,717 A | 7/1991 | Brooks | |
| 5,458,653 A | 10/1995 | Davidson | |
| 5,766,261 A | 6/1998 | Neal et al. | |
| 5,800,560 A | 9/1998 | Draenert | |
| 6,096,084 A | 8/2000 | Townley | |
| 6,284,002 B1 | 9/2001 | Sotereanos | |
| 6,379,390 B1 | 4/2002 | Advani et al. | |
| 6,692,529 B2 * | 2/2004 | Shah | 623/22.13 |
| 7,104,995 B2 | 9/2006 | Crofford | |
| 2005/0256585 A1 * | 11/2005 | Park et al. | 623/23.14 |
| 2008/0200990 A1 * | 8/2008 | McTighe et al. | 623/22.42 |

* cited by examiner

Primary Examiner—Corrine M McDermott
Assistant Examiner—Jason-Dennis Stewart
(74) Attorney, Agent, or Firm—Perry E. Van Over & Associates PLLC

(57) ABSTRACT

Provided is a novel hip replacement implant system that includes a ball assembly having a ball trunnion, the ball assembly being configured as a replacement for the head of the femur and capable of being secured by the ball assembly trunnion to a calcar implant element that can be securely seated in the calcar bone of the femoral neck, thus maintaining the load transfer function of the calcar bone of the femoral neck. A method of using the device is also provided.

13 Claims, 4 Drawing Sheets

FEMORAL HEAD CALCAR LOADING PROSTHESIS

BACKGROUND OF THE INVENTION

1. Technical Field

The present invention relates to orthopedic surgery and in particular to the provision and implantation of a novel hip prosthesis. More particularly the present invention relates to a novel femoral neck hip prosthesis that is implanted into the femoral neck and is coupled to the calcar bone of the femoral neck.

2. Background Art

In the United States approximately 500,000 hip replacements are performed on patients with hip arthritis. As the population ages and increases the number of hip replacement procedures can be expected to increase by 10 percent per year over the next decade.

The majority of hip replacements have conventionally included the replacement of the proximal portion of the femur with an elongate, often curved shaft that extends into the medullary canal of the femur. This design typically places unnatural stresses on the femur, which lead to pain and the consequent curtailment of activity for the patient. In addition to imposing unnatural stresses on portions of the femur, the negative effects of stress shielding of the portions of the femoral bone that normally carry the load transfer can result in bone weakness, fractures, and the need for subsequent revisions. It is also possible that with conventional hip replacement surgery the resulting leg length can be changed from the natural length, which can induce further gait, balance, back, and other problems for the patient. Because of the inducement of additional problems including subsequent hip fractures, the current designs of hip prosthesis often have a useful life less than that of the patient. This is particularly a problem for active, young patients.

Young patients with hip disease or injury presently have two options for hip replacement surgery, Total Hip Replacement and Surface Replacement. Total Hip Replacement requires the placement of a femoral prosthesis into the femoral canal and replacement of the acetabulum. The femoral prosthesis is fixed into the intramedullary canal of the femur at a level below the trochanteric region. This area of the femur is known as the isthmus. The isthmus provides a reproducible area for locking of the implant; however, by intrusively violating the femoral canal the options for revision surgery at a future date are limited. If revision surgery is required, it usually involves implanting a longer femoral prosthesis into the canal, a technique that is more difficult and less reproducible. Total Hip Replacement requires conventional open surgical techniques with resultant blood loss, pain, and prolonged recovery periods. Younger patients are more likely to have failure of their primary replacement procedure due to the increased mechanical demand of their active lifestyle and from a longer life expectancy standpoint. Faced with the prospect of a first, a second, and possibly more revisions over their lifetime, the Total Hip Replacement for a young patient is not a good first option. The prospect of leg lengthening of an average of 1 centimeter in Total Hip Replacement techniques is also a poor prospect for the young, active patient.

The second option for young patients, Surface Replacement is a technique for providing a contoured cap implant on the surface of the femoral head. This technique avoids the instrumentation of the canal and thus is less invasive. Surface Replacement has been considered to be the best option for active, young patients. If this preferred option fails, the young patient can then be treated with a total hip replacement. Surface Replacement of the hip does involve certain difficulties and subsequent problems for the patient. The surgical implant, which overlays the head of the femur must be precisely placed. There is a 2 to 4 percent failure rate of Surface Replacement implants due to imprecise placement. There is also a 2 to 4 percent failure of the implant due to vascular problems with the underlying femoral head. The vascular problems typically lead to collapsing of the femoral head. U.S. Pat. No. 4,332,036 issued to Sutter et al. provides an example of prosthesis with a cap over the head of the femur. While preserving a good portion of the calcar bone and avoiding the negative effects of medullary instrumentation attendant to the Total Hip Replacement techniques, the cap implant of Sutter et al. is still subject to the Surface Replacement problems discussed above.

While conventional implants have addressed the articulating needs of the hip joint, they typically have not addressed, and more often have exacerbating the stress loading problems of the hip. The Total Hip Replacement techniques have typically imposed unnatural stresses on the shaft of the femur into which the femoral prosthesis is implanted. The calcar is the hips natural bone dense area on the medial neck of the femur. It begins beneath the femoral head and travels along the medial neck to the level of the isthmus. The body lays down new bone in certain areas as a natural response to stress. The load transfer stresses through the hip are naturally carried from the femoral head to the long shaft of the femur by the calcar bone. The standard technique of removal of the neck of the femur and the instrumentation of the femur through the isthmus portion effectively guts the calcar bone in these regions and thus positions the patient for subsequent bone weakness, fractures, and the need for revision surgery. An example of this invasive and calcar destructive technique is shown in U.S. Pat. No. 5,035,717 issued to Brooks. The femur is prepared to receive the implant by cutting through the neck of the femur and instrumenting a large portion of the remaining calcar to receive the stem of the implant. Having thus removed or damaged the majority of the load transferring calcar bone, the technique attempts to transfer the load through the hip by providing a collar that overlays the cut surface of the femur and serves only to apply the stress loading in an unnatural way. Even in techniques which involve only femoral head replacement, much of the calcar bone is lost in the surgical process and the replacement head is fixed to the bone by a lateral plate, sometimes called a Thrust Plate, or by cementing small diameter stems into the medullary canal of the neck or by securing the head to the neck of the femur by use of a securing rod or post that extends completely through the load transferring calcar and anchored to the exterior of the femur. An example of the latter technique is shown in U.S. Pat. No. 7,104,995 issued to Crofford. The implant and technique of Crofford requires that the core of the load transferring calcar be bored completely through to provide passage for a fixation prosthesis, a post, which rather than using the natural strength of the calcar bone attempts to replace it with the post that passes completely through the calcar and terminates with an anchor on the exterior lateral wall of the femur. None of the conventional hip replacement techniques utilize the natural load transferring calcar bone in the neck of the femur as a loading/fixation system for the replacement implant.

For these reasons there remains a need for a hip replacement implant and technique that not only reproduces the articulation aspects of the hip joint but also utilizes the natural load transferring calcar bone of the femur so as to provide a hip replacement that avoids the shortcomings of conventional hip replacement implants and techniques and thus reduces the likelihood of subsequent failures and required revisions.

SUMMARY OF THE DISCLOSURE

The present invention meets the above identified need by providing a novel hip replacement implant system that includes a ball assembly having a ball trunnion or trunnion, the ball assembly being configured as a replacement for the head of the femur and capable of being secured by the ball assembly trunnion to a calcar implant element that can be securely seated in the calcar bone of the femoral neck.

Also provided is a novel hip replacement implant system that includes a ball assembly, a calcar implant element, and an acetabular component, the ball assembly having a ball trunnion and being configured as a replacement for the head of the femur and capable of being secured by the ball assembly trunnion to the calcar implant element that can be securely seated in the calcar bone of the femoral neck, the acetabular component being configured to be implanted in the hip of a subject and to articulate with the ball assembly.

Also provided is a novel hip replacement implant that includes a ball assembly having a ball trunnion and being configured as a replacement for the head of the femur and capable of being secured by the ball assembly trunnion to a calcar implant element that can be securely seated in the calcar bone of the femoral neck, the ball assembly including an articulating ball element that is truncated on an underside and from which underside the ball assembly trunnion extends Also provided is a novel hip replacement implant that includes a ball assembly having a metal ball element configured as a replacement for the head of the femur and a metal acetabular component, sized and configured to be implanted in the hip of a subject and to articulate with the metal ball element, the metal ball element.

Also provided is a method of implanting a hip replacement, the method including providing a hip replacement implant that includes a ball assembly having a ball element, the ball assembly being configured as a replacement for the head of the femur, a calcar implant element, and an acetabular component that is sized and configured to be implanted in the hip of a subject and to articulate with the ball element, removing the head of the femur, preparing a receiving cavity in the calcar bone of the neck of the femur leaving the calcar bone intact below the receiving cavity, implanting the calcar implant element into the receiving cavity in the neck, securing the ball element to the calcar implant.

Also provided is a method of implanting a hip replacement assembly using minimally invasive surgical methods.

Also provided is a kit containing a novel hip replacement assembly including a ball element configured as a replacement for the head of the femur and an acetabular component configured to be implanted in the hip and to articulate with the ball element.

BRIEF DESCRIPTION OF THE DRAWINGS

The foregoing and other features of the disclosed device will become apparent to one skilled in the art to which the present invention relates upon consideration of the following description of exemplary embodiments with reference to the accompanying drawings, wherein.

DETAILED DESCRIPTION OF PREFERRED EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

Figure 1:
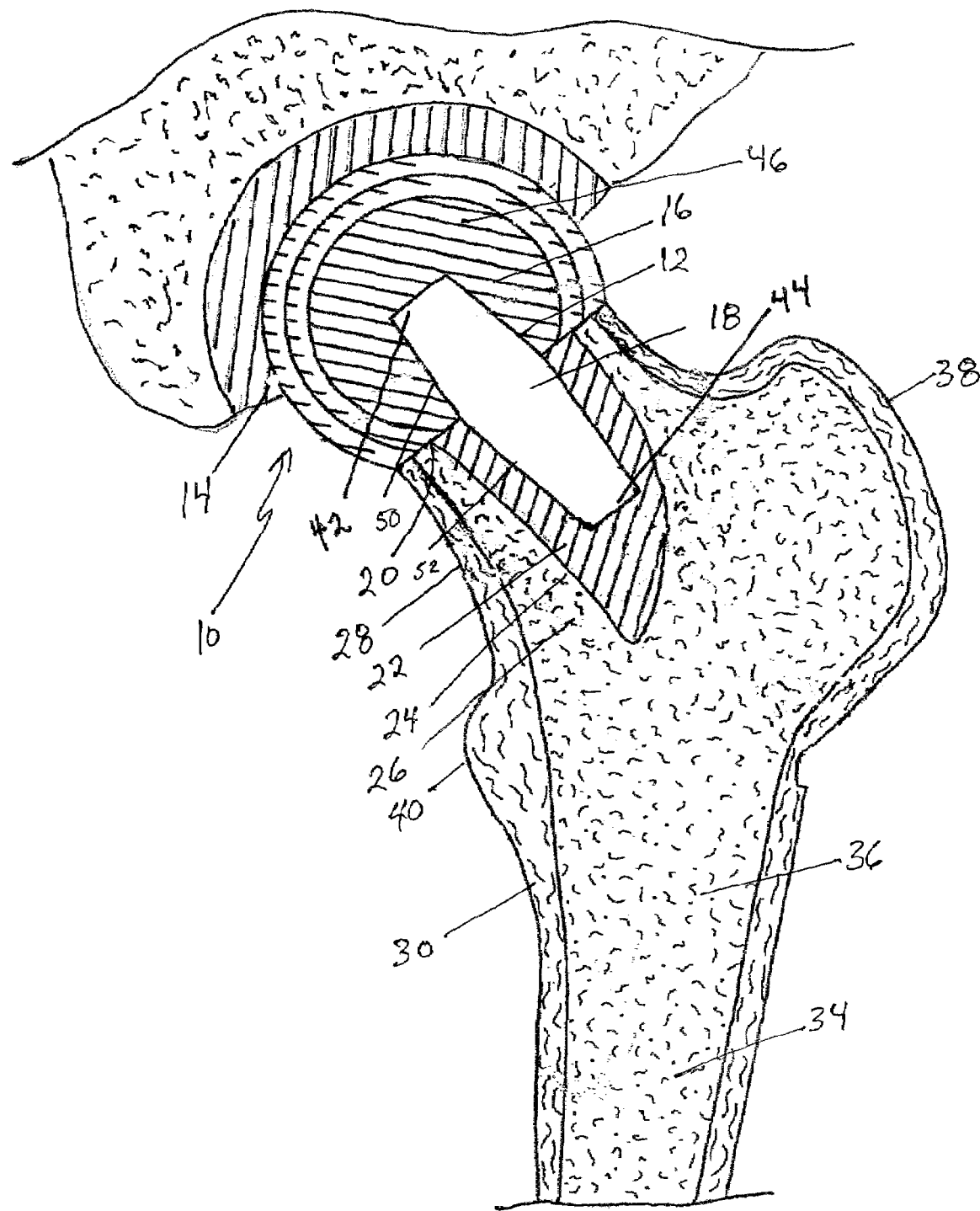
FIG. 1 shows a cross-sectional view of the hip replacement implant system including a novel femoral head calcar loading prosthesis implanted in the calcar bone of the femoral neck and the acetabulum component with which the ball assembly of the calcar loading prosthesis articulates.

The novel hip replacement implant system, as generally shown at 10 in FIG. 1 includes a femoral head calcar loading prosthesis 12 that articulates with an acetabulum replacement component 14. The femoral head calcar loading prosthesis 12 includes a ball assembly 16 and a ball assembly trunnion 18, which projects outwardly from the underside 20 of the ball assembly 16. Preferably the first end 42 and the opposing second end 44 of the ball assembly trunnion 18, as shown in FIG. 1, is provided with a Morse taper at the first end 42 extending into the body of the ball assembly 16 and at the second end 44 extending into the calcar implant element 22.

The ball assembly 16 includes an articulating ball 46, which is configured to articulate with the acetabulum 14 secured to bone of the hip. Preferably, the ball 46 and the acetabulum 14 are both metal providing a metal on metal hip articulating joint. However, it is within the concept of the invention to employ any suitable material for the ball 46 as is known in the art to provide a strong, reliable hip joint articulating assembly. Non-limiting examples of such alternative balls that can be employed in the practice of the present invention include ceramic and ceramic steel laminates. The preferred metal for use in the device is chrome cobalt alloy; however, any other metal or metal alloy suitable for use in surgical implant devices can be employed without departing from the concept of the invention.

Figure 2A:
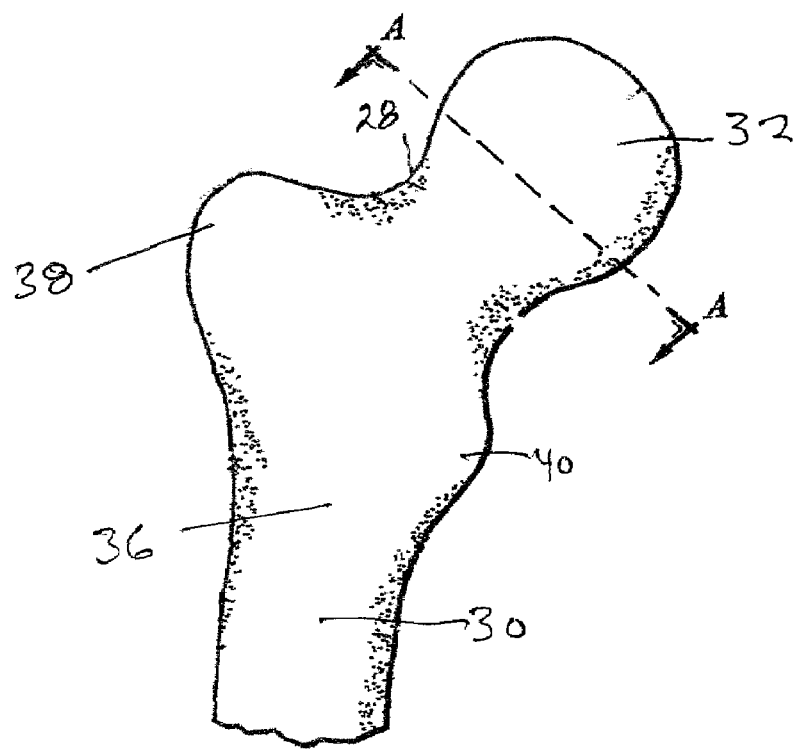
FIG. 2A shows a front view of an upper portion of a human femur with a sectional line A-A at the level where the head of the femur meets the femoral neck.
Figure 4:
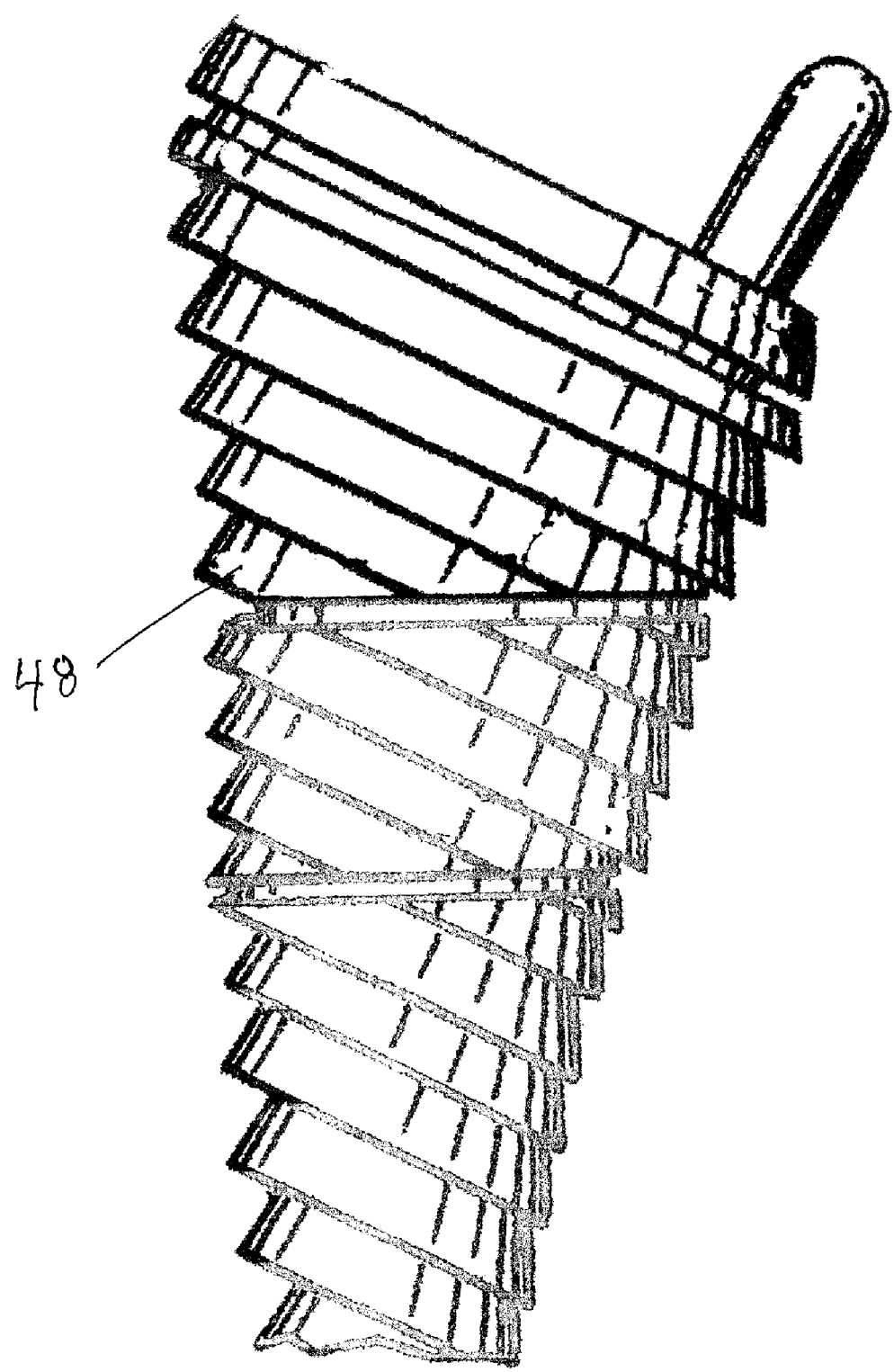
FIG. 4 shows an example of a broach that could be used or adapted for use in the method of preparation of a receiving cavity for the calcar implant element in the calcar bone of the femoral neck.

A calcar implant element 22 is provided as a wedge shaped structure having a configuration that conforms to the shape of a receiving cavity 24 that can be surgically formed using only a broach in the calcar bone 26 of the femoral neck 28. FIG. 4 shows an example of a broach 48 that is suitable for use or for adaptation for use in the method of the present invention. As shown in FIGS. 1 and 2A, the femoral neck 28 is that portion of the femur 30 immediately below the femoral head 32 and above the region of the intramedulary canal 34. In the method of the present invention, the femoral head 32 is resected at a level on the femoral neck located immediately below the femoral head 32. The calcar bone 26 is the hips natural bone dense area in the neck 28 of the femur 30. It begins beneath the femoral head 30 and extends along the medial neck 28 of the femur 30 to the level of the isthmus 36, a level beginning below the position of the greater trochanter 38 and the lesser trochanter 40 and directly above the level of the intramedullary canal of the femoral shaft. Conventional techniques of femoral head replacement require that the replacement is either fixed to the bone by a lateral plate system, a Thrust Plate, or by cementing small diameter stems into the medullary canal of the femoral neck 28. Common to all conventional implants and methods for providing a hip replacement, the calcar bone 26 of the femoral neck 28 is almost completely disrupted and destroyed or at least bored entirely through so as to provide needed space within the femur for a mechanical implant that is intended as a replacement for the natural load transferring calcar bone 26. The described implant and method of U.S. Pat. No. 6,284,002, issued to Sotereanos, is typical of the calcar destructive approach employed in conventional hip replacement technology. Unlike those conventional techniques, the present invention utilizes rather than destroys the natural load transferring calcar bone 26 in the femoral neck 28 thus avoiding the negative effects of stress shielding such as bone loss, fractures, and the attendant need for revisions. By resecting the head 32 of the femur 30 just below the head 32, the load transferring calcar bone 26, which starts at the proximal end of the femoral neck 28, is virtually intact and still well capable of transferring load stresses through the hip joint. The present invention method, using a broach only instrumentation of the calcar bone 26 of the neck 28, serves to preserve a large portion of the calcar structurally and functionally intact while still providing the necessary strength of bonding between the device of the present invention 10 and the natural bone of the patient.

Figure 2B:
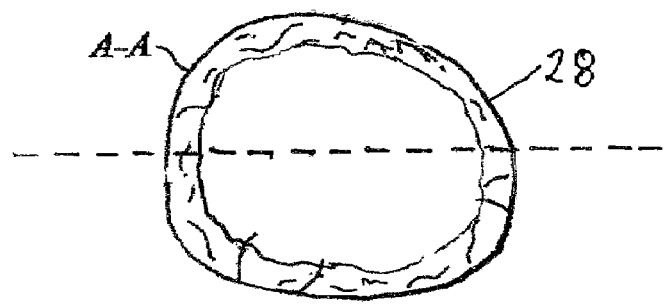
FIG. 2B shows an oblong cross-sectional view A-A of the femoral neck; the level at which the head is resected prior to implanting the hip replacement implant system of the present invention.
Figure 3A:
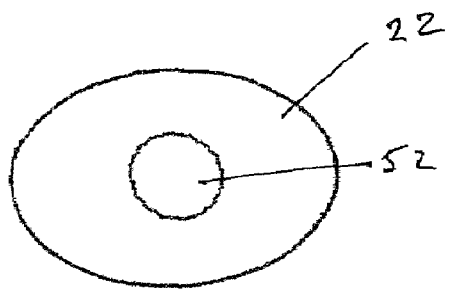
FIG. 3A-D show cross-sectional views of non-limiting examples of possible embodiments of the calcar implant element of the present invention, each of the examples having an oblong cross-sectional configuration that generally conforms to the oblong configuration of the femoral neck just below the head of the femur.
Figure 3B:
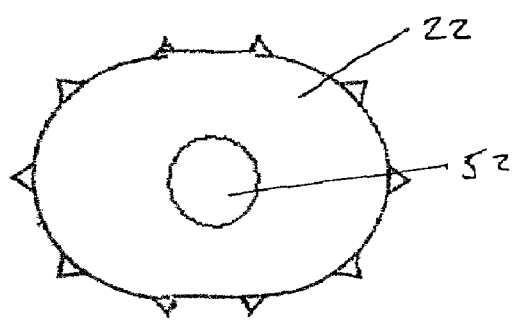
Figure 3C:
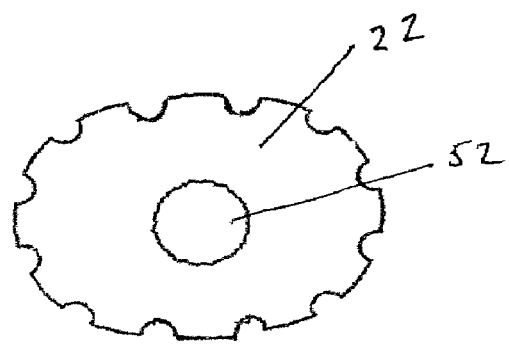
Figure 3D:
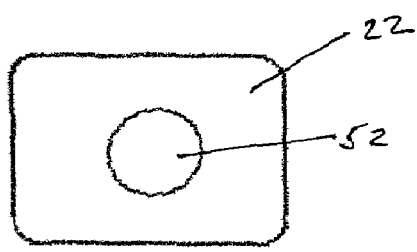

The method of the present invention can be carried out as a minimally invasive technique employing a common trochar through which the head 32 of the femur 30 can be resected just above the neck 28 as shown in FIG. 1. Section line A-A of FIG. 2A shows the approximate level on the neck 28 at which the head 32 is resected according to the present invention. FIG. 2B shows a cross-section of the neck 28 at section line A-A of FIG. 2A. As seen in FIG. 2B, the cross section is generally oblong with the greater diameter being medial-lateral. The cross-sectional configuration of the calcar implant element 22 conforms to this generally oblong shape of that portion of the neck 28 into which the calcar implant element 22 will be secured. In the minimally invasive method of the invention the receiving cavity 22 can be prepared in the calcar bone 26 of the neck 28 using only a broach 48. The cavity 24 and the calcar implant element 22 have generally conforming wedge shapes along their respective longitudinal axes. As indicated above and as best shown in the cross-sectional views of FIG. 2B and FIG. 3A-D, cavity 24 and the calcar implant element 22 also have conforming oblong shapes. This like conformation of the cavity 24 and the calcar implant element 22 provides a strong, secure, mechanical attachment without the need for bone cement or other adhesives. It is, however, within the scope of the invention to use bone cement or adhesives if determined necessary to maintain a strong attachment of the calcar implant element 22 within the cavity 24. The calcar implant element 22 can be provided with a porous coating as is well known in the art so as to promote the ingrowth of new bone from the calcar bone of the cavity 24 on to the surface of the calcar implant element 22.

Similarly, if necessary the connection of the first end 42 and the second end 44 of the trunnion 18 respectively within the ball trunnion receptacle 50 and the calcar implant trunnion receptacle 52 can be secured using any suitable adhesive known in the art.

The inventors have contemplated that each of the components of the present invention can be provided in different sizes and configured so as to be interchangeable thus permitting the surgeon to make a best fit for the particular anatomy of the patient being treated.

The device 10 can be manufactured as integral components by methods known in the art, to include, for example, molding, casting, forming, extruding, and machine processes. The components can be manufactured using materials having sufficient strength, resiliency and biocompatibility as is well known in the art for such devices. By way of example only, suitable materials can include implant grade metallic materials, such as titanium, cobalt chromium alloys, stainless steel, or other suitable materials for this purpose.

It is also within the concept of the present invention to provide a kit, which includes at least one of the novel implant devices disclosed herein. Implants of different sizes can be provided in the kit to permit selection and substitution of implants of the correct size as needed. Additionally, a kit can include tools and/or instruments suitable to facilitate implanting the device. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A novel hip replacement implant system the system comprising:
   a ball assembly comprising a solid ball and a separate trunnion, said trunnion having a first end and a second end and said ball having an upper curved surface and a lower flat surface, said lower flat surface defining an inwardly directed ball trunnion receptacle, said ball trunnion receptacle being complementary sized and configured to receive said first end of said trunnion; and
   a calcar implant element configured to be securely implanted into the calcar bone of the femoral neck of a subject, said calcar implant element having a first end and a second end, said first end defining a calcar implant trunnion receptacle sized and configured to receive said second end of said trunnion;
   wherein said calcar implant element is sized and configured to be implanted in the upper portion of the femoral neck calcar bone so as to leave intact the load transferring calcar bone of the femur.

2. The system of claim 1, further comprising an acetabular component that is sized and configured to articulate with said ball, said acetabular component being capable of being securely attached to the hip socket of a subject.

3. The system of claim 1, wherein said ball is metal.

4. The system of claim 3, wherein said acetabular component is metal.

5. The system of claim 1, wherein said trunnion has a Morse taper in the direction of each of said first end and said second end.

6. The system of claim 1, wherein said ball is selected from a group of ball manufactured from the group of materials consisting of titanium, steel, cobalt chromium alloys, ceramic, and layered metal and ceramic.

7. The system of claim 1, said calcar implant element comprising a porous coating.

8. A femoral head calcar loading prosthesis, comprising:

a ball assembly, said ball assembly comprising a solid ball and a separate trunnion, said trunnion having a first end and a second end and said ball having an upper curved surface and a lower flat surface, said lower flat surface defining an inwardly directed ball trunnion receptacle, said ball trunnion receptacle being complementary sized and configured to receive said first end of said trunnion, said ball being configured to be capable of articulation with a natural acetabulum of a subject or with a manufactured acetabulum replacement;

a calcar implant element configured to be securely implanted into the calcar bone of the femoral neck of a subject, said calcar implant element having a first end and a second end, said first end defining a calcar implant trunnion receptacle sized and configured to receive said second end of said trunnion, wherein said calcar implant element is implanted in the upper portion of the femoral neck calcar bone so as to leave intact the load transferring calcar bone of the femur.

9. The prosthesis of claim 8, wherein said ball is metal.

10. The prosthesis of claim 8, wherein said acetabular component is manufactured and is configured to be capable of being implanted as an acetabulum replacement in the hip socket of a subject.

11. The prosthesis of claim 8, wherein said trunnion has a Morse taper in the direction of each of said first end and said second end.

12. The prosthesis of claim 8, wherein said ball is selected from a group of ball manufactured from the group of materials consisting of titanium, steel, cobalt chromium alloys, ceramic, and layered metal and ceramic.

13. The prosthesis of claim 10, said calcar implant element comprising a porous coating.

* * * * *